United States Patent [19]

Coffin, Jr. et al.

[11] Patent Number: 4,677,855
[45] Date of Patent: Jul. 7, 1987

[54] METHOD FOR MEASURING DAMAGE TO STRUCTURAL COMPONENTS

[75] Inventors: Louis F. Coffin, Jr.; Thomas A. Prater, both of Schenectady, N.Y.

[73] Assignee: Electric Power Research Institute, Inc., Palo Alto, Calif.

[21] Appl. No.: 810,628

[22] Filed: Dec. 19, 1985

[51] Int. Cl.[4] .......................................... G01N 19/00
[52] U.S. Cl. ...................................................... 73/799
[58] Field of Search ................................. 73/799, 786

[56] References Cited

U.S. PATENT DOCUMENTS

| | | | |
|---|---|---|---|
| 4,003,246 | 1/1977 | Cain | 73/799 |
| 4,149,406 | 4/1979 | Russenberger | 73/799 |
| 4,452,087 | 6/1984 | D'Antonio | 73/786 |

OTHER PUBLICATIONS

Catlin, Lord, Prater and Coffin, "The Reversing DC Electrical Potential Method", Automated Test Methods for Fracture and Fatigue Crack Growth, *ASTM*, STP877, Philadelphia 1985, pp. 67–85.

Prater, Catlin and Coffin, "Application of the Reversing DC Electrical Potential Technique to Monitoring Carck Growth in Pipes", CRD Report No. 85CRD095, Jun. 1985.

Novak and Rolfe, "Modified WOL Specimen for $K_{iscc}$ Environmental Testing", *Journal of Materials*, vol. 4, pp. 701–728, 1969.

Taka, Pasis and Irwin, "The Stress Analysis of Cracks Handbook", Del Research Corp., Hellertown, Pa, 1973, pp. 29.3, 29.4.

Klintworth, "Fatigue Crack Propagation in High Strength Low-Alloy Steel Using an Electrical Potential Method", M. Sc. Thesis, Imperial College of Science and Technology, University of London, Oct. 1977.

Editor: General Electric Company, "Electric Potential Drop Monitor", Operating and Instruction Manual.

*Primary Examiner*—Stewart J. Levy
*Assistant Examiner*—Robert R. Raevis
*Attorney, Agent, or Firm*—William H. Steinberg; James C. Davis, Jr.; Paul R. Webb, II

[57] ABSTRACT

A method is provided for measuring crack growth within a material utilizing reversing d.c. potential measurements across a preformed crack. Preferably, the material is representative of structural components of interest and the material is located within the aggressive environment of such components. The measured values are plotted versus distance to obtain intercept values. These intercept values correspond to the depth of the crack at the time the measured values were obtained.

14 Claims, 1 Drawing Figure

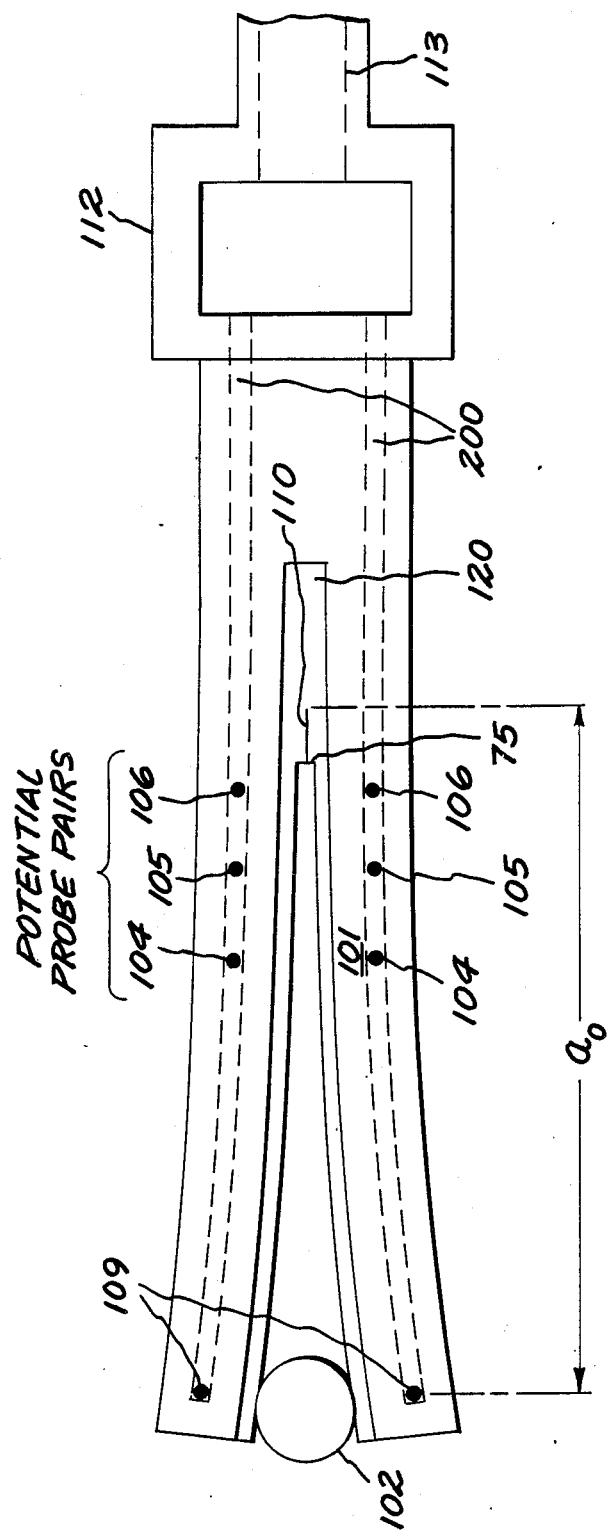

METHOD FOR MEASURING DAMAGE TO STRUCTURAL COMPONENTS

BACKGROUND OF THE INVENTION

This invention is directed to a method for measuring and monitoring damage to structural components within their environment. More particularly, it is directed to a method for measuring damage to structural components caused by stress corrosion cracking.

Exposing structural materials to aggressive environments under steady or cyclic stress can give rise to damage in the form of cracking. This is often referred to as "stress corrosion cracking" or "corrosion fatigue". Stress corrosion cracking of structural materials in aggressive environments is a continuing problem in many industries. It has been particularly so in the nuclear industry where structural materials operate under sustained or cyclic stress in high temperature water, such as that employed in boiling water reactors.

In general, the performance of structural components is predicted in advance from information on the expected loadings and resulting stress from these loadings. Although these predictions are sufficiently accurate to predict service performance, it has been found difficult to predict the lifetime of such performance due to the uncertainty in the environmental conditions and the influence thereof on stress corrosion cracking which results.

An example of the uncertainty of lifetime predictions for structural materials is the stress corrosion cracking which has been found to occur in stainless steel piping used in the nuclear industry. Although designs for new plants attempt to compensate for this phenomenon, it is desirable to monitor and assess the extent of damage in plants which have been operating for a number of years to help predict their lifetimes and possibly extend their lifetime. Methods for assessing the state of damage have been directed towards monitoring the aggressive environment. In the case of boiling water reactors, the water chemistry is measured to determine factors such as resistivity, electrochemical potential, oxygen level and impurity levels. Such measurements are indirect. No direct measurement is made of the effect this water chemistry has on crack growth in the structural materials during plant service. Therefore, the extent to which the lifetime of the structural material is extended by varying operating condition is unknown.

Methods for directly measuring crack growth in specimens removed from their environment have been disclosed over the years. These methods use a variety of monitoring systems including visual and voltage potential drop methods, such as that disclosed by Beevers, Editor, "The Measurement of Crack Length and Shape During Fracture and Fatigue", Engineering Materials Advisory Services, Limited, (1980). However, to measure the crack growth of plant structural components in their environment, an accurate method and apparatus are needed. Accurate measurements of crack growth through potential drop methods have not been obtained previously due to deficiencies in relating voltage measurements to crack size and deficiencies in the equipment utilized. This invention overcomes these difficulties and is capable of measuring crack growth in such environments to within about ±0.0001 inch.

SUMMARY OF THE INVENTION

A method for measuring crack growth within a solid is provided wherein said solid, having a preformed crack, is exposed to an aggressive environment while applying a load to the solid sufficient for the crack to grow. A current is passed through the solid to establish a voltage drop across the crack. This voltage is measured by at least two pairs of probes positioned at up to 99% of the preformed crack depth. The two members of each pair of probes are positioned on opposite sides of the crack at equal, known distance from the mouth of the crack. The measured voltage across each pair is plotted versus the distance from the crack mouth of each probe pair. A "best fit" straight line of voltage versus distance from the crack mouth is passed through these points and extrapolated to obtain the distance intercept of said line at the axis where voltage =0. The changes in value for the intercept are monitored over time to determine the change in crack depth.

OBJECTS OF THE INVENTION

An object of the present invention is to provide a method and apparatus for measuring and monitoring damage to structural components within their environment over extended periods of time.

Another object of the present invention is to provide a method for measuring the instantaneous and accumulated damage to structural components.

A further object of the present invention is to provide a method for measuring growth in cracks as small as 0.0001 inch.

DESCRIPTION OF THE DRAWING

The FIGURE is a schematic representation of a sensor, having a double cantilever beam geometry, which can be used in the process of this invention.

DETAILED DESCRIPTION OF THE INVENTION

This invention is directed to a method for measuring crack growth within a solid. Embodiments of this invention can be used to determine damage to structural components within their environment due to stress corrosion cracking. This is accomplished by measuring and monitoring the electric potential drop across a preformed crack within a solid material of interest, herein referred to as a "sensor". When a current is caused to flow through the sensor perpendicular to the crack, the potential difference between two points located on opposite sides of the crack will increase as the size of the crack increases. Measurement of the electric potential will provide information as to the instantaneous damage as well as the accumulated damage to the sensor in the form of crack growth.

Crack growth is preferably measured in a solid material of interest or sensor. The solid must be electrically conductive, such as carbon or alloy steel, nickel and nickel based alloys, titanium and its alloys and nuclear structural materials such as austenitic stainless steels, Inconel TM and the like. This is necessary to obtain measurements of the electric potential across the preformed crack. In the preferred embodiments of this invention, the sensor provides information that reflects on the condition of a particular structural component of interest. To achieve this purpose, it is preferable to manufacture this sensor from the same material with the same process history as the structural components of interest. The size and shape of the sensor can vary widely. Certain sizes and shapes may be preferred to enhance compactness, durability, sensitivity, simplicity of installment or flexibility.

The preformed crack within the solid is of a known depth, designated herein as $a_o$. This preformed crack defines the site where electric potential measurements are taken. Therefore, it is desirable to position the crack at a location on the sensor convenient for taking electric potential measurements at multiple points. The size and shape of the preformed crack can vary widely; however, the cracks cannot be of a size so as to separate the sensor into two sections. The crack is defined as possessing a mouth and a tip. The "mouth of the crack" is defined herein as the point or line of action of load application. The "crack tip" is the leading edge of the crack. The "depth" of the crack is defined herein as the distance from the mouth of the crack to the crack tip. The initial depth of the preformed crack is defined herein as $a_o$.

Although the sensor size, crack size and crack location can vary widely, the configuration of the sensor preferably permits a load of sufficient magnitude to be applied to the crack to provide a crack tip stress intensity factor that will allow the crack to grow at an appropriate rate. In addition, it is preferable for the configuration of the sensor to permit measurement of the electric potential at multiple points along the crack. A configuration which permits a load of sufficient magnitude to be conveniently applied is that of the sensor shown in the figure having a "double cantilever beam" geometry. This geometry is defined herein as having two parallel arms (beams) joined at one end and separated at the other. A slot or deep notch separates each member and the base of this notch is referred to as the notch root. The preformed crack is preferably positioned at the notch root. This compact shape provides high flexibility and high sensitivity. This configuration permits a number of measurements to be taken at various positions along the two beams since the effective crack depth is extended along these beams. In addition, if the load remains constant, the stress intensity factor at the crack tip increases as the distance between the crack tip and the point of the load increases. Therefore, the long length of the sensor permits the threshold crack tip stress intensity to be obtained at low load levels. Loads sufficient for the crack to grow can be obtained by simply placing a wedge between the two beams.

The level of stress at the tip of a sharp crack in a solid is characterized by the stress intensity factor. For the preformed crack to grow, it must experience a minimum or threshold stress intensity factor at the crack tip. The stress intensity factor is dependent on many variables including the geometry or configuration of the body and the loading conditions. The stress intensity factors for various configurations and loadings have been catalogued by Sih, G.C., *Handbook of Stress Intensity Factors*, Institute of Fracture and Solids Mechanics, Lehigh University, Bethlehem, Pa. 1973; Tada., Paris, P.C. and Irwin, G.R., *Stress Analysis of Cracks Handbook*, Dell Research Corporation, Hellertown, Pa. 1973 and Sih, G.C., Ed., *Methods of Analysis and Solutions of Crack Problems*, Noordhoff (1973). These references also provide numerical solutions of the stress intensity factor for various test specimens, i.e., sensors, and are incorporated herein by reference. In particular, a detailed analysis of calculating the stress intensity factor for the double cantilever beam geometry shown in the figure is given by Tada, Paris and Irwin at pages 29.3 and 29.4 of the reference described above for either an applied load or a fixed displacement. The numerical solution of the stress intensity factor can be represented by the general formula $K_I = $ (applied stress) $\times$ (crack length)$^{\frac{1}{2}} \times (Y)$ where Y is a parameter representing the crack and specimen geometry including variables such as the width of the body and the distance of the crack from the surface. In the special case of the geometry shown in the figure, the stress intensity factor reduces to the relationship given by Tada, Paris and Irwin referenced above.

The minimum or threshold stress intensity factor which permits the crack to grow is dependent on the composition of the body and the environment to which it is exposed. The threshold stress intensity factors for various materials have been studied widely. Threshold stress intensity factors for aluminum, copper alloys, ferritic steel and titanium alloys are discussed in Arup and Parkins, Ed., *Stress Corrosion Research*. NATO Advanced Study Institute, Sijhoff and Noordhoff, Alphen aan den Irjn, The Netherlands (1979). The teachings of this reference are incorporated herein by reference. Where the threshold stress intensity factor for the material used in the sensor is known or determined, the minimum load necessary to obtain this threshold value at the crack tip can be calculated for the configuration of the sensor by the analyses described above.

When monitoring a structural component, it may be desirable to apply a load that will match the stress intensity experienced by said component within the sensor. If this level of load is below the threshold stress intensity factor, it is preferable to either match the threshold stress intensity factor or exceed it slightly. Where the stress intensity is not known or the threshold stress intensity factor for the solid is unknown, excessive loads may be applied to the crack to insure its growth. Such a practice will not significantly interfere with measurement of the crack growth. However, applying excessive loads to the sensor increases the bending stress in the arms of the sensor and may lead to plastic deformation or stress relaxation. When attempting to determine damage to structural components, it is preferable to avoid such phenomena. To prevent deformation of the sensor, it is often preferable to minimize the bending stress while obtaining the desired stress intensity factor. For the double cantilever beam geometry, this is accomplished by maximizing the beam height and by introducing side grooves of appropriate depths on the plane of the preformed crack.

Another advantage to placing side grooves within the sensor along the plane of the preformed crack is that these grooves determine the plane in which the crack grows. It is important to keep the fracture surfaces of the crack as planar as possible to avoid multiple cracking and bridging of the crack. Bridging can lead to a short circuit in the current flow and cause errors in the electric potential measurements.

For monitoring stress corrosion cracking in aggressive environments, an active load or a fixed displacement is required. The means for applying a fixed displacement to cause the preformed crack to grow can be a simple wedge forced within the slot to expand the crack. Other means are also suitable, such as a clamp, bolt or similar means which expands the crack. The means for applying a fixed displacement must be comprised of a material which is electrically non-conductive and it is preferred that such material have a thermal coefficient of expansion which matches that of the sensor material. This helps maintain a nearly constant stress intensity factor at the crack tip under changing temperatures. Where the sensor is to be placed within an aggressive environment, it is essential that the material utilized to apply the fixed displacement be resistant to such aggressive environments.

In the preferred embodiments of this invention, the sensor, having a preformed crack, is placed within an aggressive environment. The term "aggressive environment", as used herein, refers to those environments which attack the material of which the sensor is comprised, such attack being of sufficient magnitude to enhance the growth of the preformed crack. When monitoring the damage to a structural component, the sensor is placed within the same environment as the structural component. The sensor then experiences the same changing environmental conditions as these structural components. Conventional methods and devices can be used to support the sensor in these environments.

The growth of the crack is monitored preferentially by reversing d.c. potential methods. To accomplish this, a reversing direct current is applied to the sensor so as to provide a potential field within the sensor. It is noted that the use of a reversing d.c. potential is not essential to practice this invention. Any means for producing a potential in the sensor is suitable. This can be accomplished by simply applying a current to the sensor. The probe voltage can fall within a wide range, i.e., from about 0.1 microvolts to 12 volts. However, it is desirable to maintain the potential in the microvolt range to avoid excess noise and drift and to minimize electrochemical influences on crack growth. These factors will detract from the accuracy of the measurements obtained.

Where it is desirable to maintain the potential in the microvolt range, it may be necessary to amplify the electric potential measurements obtained across the probes. Amplification as much as 100,000 times or more may be necessary to permit measurement of the electric potential field within the microvolt range. Where utilizing amplifiers, those which experience low long-term drift, i.e., less than 2 microvolts per year, are preferred. Where such an amplifier is used, the period for current reversal is often limited by the settling time of the amplifier. A $\frac{1}{2}$ second reversal period is adequate for some 1000× gain amplifiers.

Two leads are required to supply the current to the sensor. The current leads are typically attached at or near the furthest point from the crack tip of the preformed crack.

The current can be supplied to the material by conventional leads such as a wire, cable, bus and the like. These leads can be attached to the sensor by conventional techniques which permit current flow through the sensor, such as spot welding, brazing, riveting, soldering, wrapping and the like. Where the sensor is to be inserted in an aggressive environment, such as high pressure, high temperature water, it is desirable to insulate the potential probes and current leads. For example, Teflon ® (Dupont) shielded platinum is preferred for use in high pressure, high temperature boiling water environments.

The current is preferably reversed periodically to avoid amplifier zero drift and drift due to thermal electromotive forces created at the junction points for the current leads. Measurements made with reversed direct current avoids the need for taking a measurement where zero voltage is supplied. By avoiding measurements at zero voltage, inaccuracies due to amplifier zero drift are eliminated. It is preferable to reverse the direct current at a rate within the range of about 0.5 to 4 times per second. Reversing the current at higher rates encourages the problems associated with using alternating current, where the voltage experience a "skin effect" in which the current density near the surface of the sensor is higher than the subsurface portions of the sensor. Reversing the current at rates lower than 0.5 times per second yields fewer potential readings resulting in lesser resolution of the crack length. The rate at which the current is reversed may be limited by the settling time of the equipment utilized, such as an amplifier. Any conventional switching device is suitable for reversing the direct current. Those devices which experience low drift characteristics, i.e., less than 0.1%, and low variances, i.e., less than 0.1%, are preferred. The switching device may be controlled by a general purpose computer or other controlling means, such as a timer.

The voltage is measured across the crack by multiple pairs of probes. At least two pairs of probes are required to perform this process; however, at least three pairs of probes are preferred for accurate measurement of the crack growth. Each pair of probes is positioned at a different distance from the mouth of the crack. The two members of each pair are positioned on opposite sides of the crack, preferably an equal distance from the plane of the crack. The two members of each pair are also equidistant from the mouth of the crack, i.e., they are the same distance from the leads which supply a current to the sensor. The probe pairs must be positioned no closer than 99% of the crack depth. This invention does encompass processes wherein extra probes are positioned at crack depths greater than 99%. However, the values obtained are ignored and only the measurements less than 99% of the crack depth are used. It is preferable to position the probes at a distance of about 25-95% of the crack depth for a sensor having a double cantilever beam geometry. It is also preferable to equally distribute the probe pairs within this range. The measurements obtained from probe pairs so positioned will provide the most useful and accurate information in determining the growth of the crack. Where the sensor is of a double cantilever beam geometry, it is also preferable to position the probes and the current leads at the neutral axis, i.e., the geometric center, of each beam. This avoids significant variations in the electric potential measurements due to increased loading on the cracks.

The potential difference across the preformed crack can be detected by conventional means capable of receiving a voltage across a pair of probes on a conductive material. The probes can be simple contacts, screws, welds and the like where a conductive lead, such as a wire, cable, bus, etc. is affixed to the sensor. Where the environment is aggressive, it is preferable to insulate these leads in the same manner as that described for the current supplying leads above. These conductive leads are affixed to the sensor in a manner which permits electrical conductance to a voltage measuring device, such as a voltmeter or an analog/digital converter.

FIG. 1 illustrates a preferred configuration for a sensor which can be used in the process of this invention. As indicated above, sensor 101 is of a double cantilever beam geometry. Preformed crack 110 is positioned at the notch root 75 of the double cantilever beam. Side grooves 120 are located on both beams, on the portions of the beams facing one another. The side grooves reduce the thickness of the portion of the beams facing each other and reduce the thickness of the region in which the preformed crack is located. The sensor is supported in the aggressive environment by pressure coupling 112. Channel 113 provides access to channels (or holes) 200, both of which provide pathways for the conductive leads attached to the probe pairs and the conductive leads which supply the d.c. potential to the sensor. The reversing direct current is supplied at points 109 and the effective depth of the crack is indicated by line $a_o$. Probe pairs 104, 105 and 106 detect the voltage across the crack. Wedge 102 applies a static load on the crack 110, providing the desired crack tip stress intensity factor.

It is preferable to measure the value of the potential difference across the probes continuously; however, intermittent measurements of the potential difference are acceptable and do provide useful information as to crack growth. It is desirable to measure the potential difference as accurately as possible so as to enhance the determination of crack growth.

To enhance the resolution of the voltage detecting step, an "average measured value" for the potential difference across each probe pair is obtained by averaging detected values. In general, the more detected values averaged, the higher the resolution.

When utilizing a reversing d.c. potential method, it is preferable to first calculate an average reading per current cycle for each probe pair from at least ten paired detected values (readings), i.e., ten readings are taken when the current is positive and ten readings are taken when the current is negative. These positive and negative readings are preferably detected within milliseconds following the setting time of the amplifier. One half the difference between the averaged positive readings and averaged negative readings is calculated and is the average reading per current cycle. In order to increase resolution, it is preferable to average readings for about 100 to 100,000 current cycles to obtain a single reading or the "average measured value". This corresponds to averaging about 1,000 to 1,000,000 paired detected values. By averaging this large number of paired detected values, the signal to noise ratio for the measured values increases. By increasing this ratio, smaller changes in the potential difference across the crack can be resolved and, therefore, smaller changes in crack size can similarly be resolved. Depending on the noise in the system, the average measured value obtained from about 10,000 paired detected values may give a crack growth determination as small as 0.0001 inch since the resolution of the process increases with the square root of the number of detected values averaged. Systems with more noise will require more detected values for the resolution sought for.

These detected values can be averaged by a general purpose digital computer or by a computer customized to provide the degree of averaging desired. In addition, a circuit which averages the detected potential difference across each pair of probes can be used in lieu of a computer.

The average measured voltage across each pair of probes may be plotted against the depth of said probes to approximate a straight line. As indicated above, the depth of the probes is the distance from the current supplying leads to the probe itself. Alternatively, a straight line may be approximated through those points by a linear regression analysis. The slope of this line, m, is calculated by a linear, least-squares fit of the input data, $(x_i, y_i)$, wherein $y_i$ is the measured voltage across a pair of probes and $x_i$ is the depth of said probes.

$$m = \frac{\left(\frac{\sum_{i=1}^{N} x_i y_i}{N}\right) - \bar{x}\bar{y}}{(\sigma_x)^2}$$

where i is a whole number of probe pairs from 1 to N, $\bar{x}$ and $\bar{y}$ are the average values for the values $x_i$ and $y_i$, respectively, and $$(\sigma_x)^2 = \frac{\sum_{i=1}^{N} x_i^2}{N} - (\bar{x})^2$$

First the intercept, b, is calculated by the formula $b = \bar{y} - m\bar{x}$, where m, $\bar{x}$, and $\bar{y}$ are as defined above. The intercept of this approximated line with the axis where voltage $=0$ is then obtained. The intercept value, I, where y is equal to zero is $-b/m = I$.

As the crack grows, the individual potential values increase and the value for the intercept increases. The changes in value for the intercept are monitored over time to determine the change in crack depth in that period of time. A 10% increase in the intercept value corresponds to about a 10% increase in crack size.

To calculate an absolute value for the depth of a growing crack, the depth of the preformed crack must be known. The intercept value for the preformed crack at this known depth must also be obtained. The ratio of the preformed crack depth to a subsequent crack depth is equivalent to the ratio of their intercept values. For example, $$I_2/I_o = a_2/a_o$$

where $a_2$ is the unknown crack depth at time $t_2$, $a_o$ is the preformed crack depth and $I_2$ and $I_o$ are their intercept values, respectively. Where an intercept value is obtained ($I_2$) the unknown crack depth ($a_2$) can be calculated by the formula below.

$$a_2 = \left(\frac{I_2}{I_o}\right) a_o$$

Other functions which correlate the intercept values to the depth of the crack are suitable and are considered to be within the scope of this invention, particularly those which operate on the preformed crack depth, $a_o$, with a coefficient derived from the intercept values $I_o$ and $I_2$, as defined above.

The intercept value for the preformed crack and the depth of said preformed crack are used in the first determination of an absolute value for a "grown" crack. Thereafter, these calculated crack depths and their intercept values can be used in lieu of the values for the preformed crack. For example, $$a_2 = \frac{I_2}{I_1} a_1$$

wherein $a_2$ is the unknown crack depth at time $t_2$, $a_1$ is a predetermined absolute value for the depth of said crack at time $t_1$ and $I_2$ and $I_1$ are the intercept values at $t_2$ and $t_1$, respectively. For simplicity, it is preferable to utilize the preformed crack depth, $a_o$, as the predetermined crack depth and its intercept, $I_o$, for all calculations. The depth of the preformed crack is predetermined by conventional measuring techniques prior to placement of the sensor in the aggressive environment.

A digital computer can calculate the values for the intercepts and perform the functions on these values to obtain data which corresponds to the depth of the crack. This data may be communicated to the user by conventional means, such as a visual recorder or by acoustic warning signals. The data may also be communicated to an automatic control mechanism and/or stored for subsequent analysis and interpretation.

The following example is provided to illustrate embodiments of this invention. It is not intended to limit the scope of the claimed invention to the embodiment described.

EXAMPLE

The sensor utilized in this example was of the general configuration illustrated in the figure of the drawing.

A Sorenson d.c. power supply capable of a current control mode with 0.02% regulation and 0.03% drift characteristics was utilized. Amperage varied between 1–5 amps. A solid state switch altered current direction and was controlled by solid state logic levels of 0/5 volt d.c. from the microcomputer described more particularly below. The current was switched at a rate of ½ second at each polarity. A shunt between the switch and d.c. power source was utilized to provide power to the microcomputer.

Two isolated Analogic Co. amplifiers (1000× gain) with high 166dB common-mode rejection and low long-term drift were connected between the microcomputer and the sensor. Pairs of copper leads (0.02" diameter) were connected to the amplifier from platinum leads connected to the sensor. Platinum wire shielded with Teflon ®(Dupont) sleeving capable of withstanding 288° C. was used to supply current to the sensor and to detect the potential difference across points on the sensor. Current was supplied with copper leads (0.040" diameter) to platinum leads (0.030" diameter, 8" long). The platinum detecting leads were 0.01" diameter and 12" long and were spot welded to the sensor at points indicated in the figure, at the depth described below. The probes were positioned on the neutral axis of each beam.

The microcomputer was Intel ® based customized to receive 16 detected values from the amplifiers every ½ second. The microcomputer provides 100× additional amplification. The microcomputer was also given the following input data so as to calibrate the monitor prior to the test: crack depth, maximum stress intensity and minimum stress intensity, number of probe pairs, the distance of said probe pairs from the mouth of the crack, the specimen dimensions and the voltage at the preformed crack depth. Data from the microcomputer was displayed by a digital voltmeter and recorded on tape.

A sensor of furnace sensitized 304 stainless steel having the configuration as illustrated in the figure was tested in an autoclave in 550° F. 200 $O_2$ppb water. The sensor was placed under a constant bending stress of 37 ksi by an active load. The sensor was held at constant load with a periodic unloading and reloading. A multi-wire cable was fed through the coupling to provide connections to the d.c. power source and the amplifiers. The three probes were positioned on the sensor at a depth ($x_i$) of 2.0 inches, 2.4 inches and 2.8 inches. The initial crack depth, $a_o$, was 3.06384 inches. The average measured voltage ($y_i$) in volts at these probe pairs for the initial crack length were, $68.6900 \times 10^{-6}$ $48.8800 \times 10^{-6}$ and $28.6400 \times 10^{-6}$. To obtain these values, 16 paired readings (detected values) were taken per second, i.e., 16 positive readings were taken in ½ second and 16 negative readings were taken in ½ second. An average reading per cycle was calculated from these readings and an "average measured value" was obtained after about 1 hour, i.e., about 3600 cycles. This corresponds to averaging about 58,000 paired detected values. The average values for these data points, $\bar{x}$ and $\bar{m}$, are 2.4 inches and $48.7367 \times 10^{-6}$ volts, respectively. The three values for $x_i$ provide a value for $(\sigma_x)^2$ of 0.10667, as shown below.

$$(\sigma_x)^2 = \left( \frac{\sum_{i=1}^{N} (x_i)^2}{N} \right) - \bar{x}^2 =$$

$$\frac{2^2 + 2.4^2 + 2.8^2}{3} - (2.4)^2 = .10667$$

The slope m was calculated as $-50.0617$ by the formula $$\frac{\left( \frac{\sum_{i=1}^{N} x_i y_i}{N} \right) - \bar{x}\bar{y}}{(\sigma_x)^2} =$$

$$\frac{\left( \frac{2 \times 68.69 + 2.4 \times 48.88 + 2.8 \times 28.64}{3} \right) - 2.4 \times 48.7367}{.10667}$$

The intercept, b, was 168.8848, as determined by $b = \bar{x}m + \bar{y}$, and the intercept value, $I_o$ is $-b/m$ (where y =0) or 3.3735.

After about 57.1 minutes under the conditions described above, the average voltage ($y_i$) for the three probe pairs were $70.7813 \times 10^{-6}$, $50.8831 \times 10^{-6}$ and $30.6787 \times 10^{-6}$, respectively. The average of these values ($\bar{y}$) is $50.7877 \times 10^{-6}$ volts. The value $(\sigma_x)^2$ is as defined above and the slope, $m_1$, was calculated as $-50.1033$ from the formula described above. The intercept, b, was 171.0356 and the intercept value, $I_1$, was 3.4137.

An absolute value for the crack depth, $a_1$, was then determined by the formula $$a_1 = a_0 \frac{I_1}{I_0} = 3.06384 \times \frac{3.4137}{3.3735}$$

which gave a value of 3.1003.

It will be obvious to those skilled in the art that variations of the above embodiments are possible without departing from the scope and spirit of this invention. It is intended that these variations be included within the scope of this invention.

What is claimed is:

1. A method for measuring crack growth within a solid having a preformed crack and a crack mouth which comprises the steps of applying a current to the solid to produce a potential field within said solid, measuring the voltage across the crack by at least two pairs of proves positioned at up to 99% of the preformed crack depth measured from the mouth of the crack, the two probes from each pair of probes being positioned on opposite sides of the crack at an equivalent distance from the mouth of the crack; approximating a straight line with average values for the measured voltage across each pair of probes versus the average distance of said pair of probes from the mouth of the crack, calculating the distance intercept of said straight line at the axis where voltage=0, and monitoring the changes in value for the intercept over time to determine the change in crack depth.

2. A method as in claim 1 wherein the current applied to the solid is reversed in polarity periodically.

3. A method as in claim 2 wherein the solid comprises a sensor having a double cantilever beam geometry and the preformed crack starting at the surface joining the two cantilever beams.

4. A method as in claim 3 wherein the current is applied near the ends of each of the cantilever beams.

5. A method as inclaim 3 wherein the voltage across the crack is measured by from 3 to 7 pairs of probes.

6. A method as inclaom 8 wherein the pairs of probes are equally spaced between 25 to 95% of the crack depth and the probes are positioned on the neutral axis of each beam.

7. A method as in claim 3 wherein the sensor is comprised of a material selected from teh group consisting of alloy steel, nickel, nickel-based alloys, titanium, austenitic stainless steel and Inconel TM.

8. A method as in claim 1 wherein a load is applied to the crack sufficient for the crack to grow.

9. A method as in claim 8 wherein the applied load is a static load.

10. A method as in claim 1 wherein the voltage is measured across each pair of probes from 10 to 20 times per second.

11. A method of continuously monitoring the instantaneous and accumulated crack growth damage of components carry cooling fluid in an operating plant comprising the steps of placing a sensor having a preformed crack and a crack mouth into the cooling fluid; applying a current to the sensor to produce a potential field within said sensor, measuring the voltage across the crack by at least two pairs of probes positioned at up to 99% of the preformed crack depth measured from mouth of the crack, the two probes from each pair of probes being positioned on opposite sides of the crack at an equivalent distance from the mouth of the crack; approximating a straight line with average values for the measured voltage across each pair of probes versus the average distance of said pair of probes from the mouth of the crack, calculating the distance intercept of said straight line at the axis where voltage =0, and monitoring the changes in value for the intercept over time to determine the change in crack depth of the sensor which is indicative of the crack growth damage of components carrying fluid in the operating plant.

12. The method of claim 11 wherein the sensor is of the same composition as the fluid carrying components.

13. A method as in claim 11 wherein the load applied provides a crack tip stress intensity factor about equal to the anticipated stress intensity factor of the components carrying the cooling fluid.

14. The method as in claim 11 wherein the sensor is comprised of a material selected from the group consisting of alloy steel, nickel, nickel-based alloys, titanium, austenitic stainless steel, and Inconel TM.

* * * * *